United States Patent
Miyake et al.

(10) Patent No.: US 11,097,999 B2
(45) Date of Patent: Aug. 24, 2021

(54) PROCESS FOR PREPARING 4-PENTEN-2-YNAL

(71) Applicant: Shin-Etsu Chemical Co., Ltd., Tokyo (JP)

(72) Inventors: Yuki Miyake, Niigata (JP); Naoki Ishibashi, Niigata (JP); Takeshi Kinsho, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/010,236

(22) Filed: Sep. 2, 2020

(65) Prior Publication Data

US 2021/0061745 A1    Mar. 4, 2021

(30) Foreign Application Priority Data

Sep. 4, 2019 (JP) .............. JP2019-160879

(51) Int. Cl.
*C07C 45/42* (2006.01)
*C07C 47/20* (2006.01)

(52) U.S. Cl.
CPC .............. *C07C 45/42* (2013.01); *C07C 47/20* (2013.01)

(58) Field of Classification Search
CPC .................................................... C07C 45/42
See application file for complete search history.

(56) References Cited

PUBLICATIONS

Chelpanova et al. Conjugated systems. CLVII. Synthesis and hydrobromination of 4-penten-2-ynal. Enyne Compounds. Zhurnal Obshchei Khimii, vol. 32, 2487-2489. CA Abstract No. 58:72891; Accession No. 1963:72891 HCAPLUS. (Year: 1962).*

Hoddle et al. "Synthesis and Field Evaluation of the Sex Pheromone of *Stenoma catenifer* (Lepidoptera: Elachistidae)" Journal of Economic Entomology, Ecology and Behavior, 102(4):1460-1467 (2009).

Jones et al. "Researches on Acetylenic Compounds. Part LX.* The Synthesis of Three Natural Poiyacetylenic Hydrocarbons" Journal of the Chemical Society (Resumed), pp. 1054-1059 (1958).

Zou et al. "Improved synthesis of (9Z)-9, 13-tetradecaclien-11-ynal, the sex pheromone of the avocado seed moth, *Stenoma catenifer*" Tetrahedron Letters, 51(9):1336-1337 (2010).

Millar et al. "(9Z)-9,13-Tetradecadien-11-ynal, the sex pheromone of the avocado seed moth, *Stenoma catenifer*" Tetrahedron Letters, 49(33):4820-4823 (2008).

Chelpanova et al. "Conjugated systems. CLVII. Synthesis and hydrobromination of 4-penten-2-ynal" Lensovet Leningrad Technological Institute, Translated from Zhurnal Obshchei Khimii, 12(8):2453-2455 (1962; Original article submitted Jul. 8, 1961).

Extended European Search Report corresponding to European Patent Application No. 20194348.7 (5 pages) (dated Jan. 22, 2021).

* cited by examiner

*Primary Examiner* — Sikarl A Witherspoon
(74) *Attorney, Agent, or Firm* — Myers Bigel, P.A.

(57) ABSTRACT

A process for preparing 4-penten-2-ynal of the following formula (2):

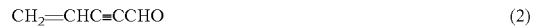

the process comprising a step of
hydrolyzing a 5,5-dialkoxy-1-penten-3-yne compound of the following general formula (1):

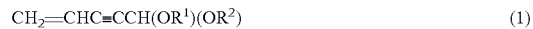

wherein $R^1$ and $R^2$ represent, independently of each other, a monovalent hydrocarbon group having 1 to 15 carbon atoms, preferably 1 to 8, more preferably 1 to 4, or $R^1$ and $R^2$ may be bonded to each other to form a divalent hydrocarbon group, $R^1$-$R^2$, having from 2 to 10 carbon atoms, to obtain 4-penten-2-ynal (2).

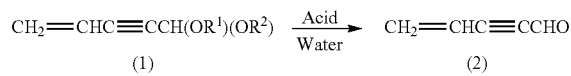

6 Claims, No Drawings

PROCESS FOR PREPARING 4-PENTEN-2-YNAL

TECHNICAL FIELD

The present invention relates to a process for preparing 4-penten-2-ynal.

BACKGROUND ART

Avocado seed moth (*Stenoma catenifer*) is a most serious pest to attack avocado fruit in the Central and South America such as Mexico, Guatemala, Peru, Ecuador, and Brazil. For instance, pesticides are sprayed 7 to 11 times in a season in some areas of the South America. Nevertheless, it is said that 60% of the fruits is damaged. One of the reasons for this is that larvae of this pest penetrate into the flesh, which makes the control with pesticides difficult. Accordingly, biological control is attracting attention, and use of a sex pheromone is thought to be promising.

A sex pheromone of *Stemoma catenifer* is a dienynal compound, (9Z)-9,13-tetradecadien-11-ynal (Non-Patent Literatures 1 and 2, listed below).

LIST OF THE PRIOR ART

Non-Patent Literatures

[Non-Patent Literature 1] Jocelyn G. Millar et al, Tetrahedron Letters. 2008, 49: 4820-4823.

[Non-Patent Literature 2] Mark S. Hoddle et al, Ecology and Behavior. 2009, 102(4): 1460-1467.

[Non-Patent Literature 3] Jones. E. R. H et al, Journal of the Chemical Society, 1958, 1054-1059.

SUMMARY OF THE INVENTION

It is considered that the terminal enyne skeleton in (9Z)-9,13-tetradecadien-11-ynal described above can be constructed from 4-penten-2-ynal having a similar skeleton. 4-Penten-2-ynal is synthesized, for example, by oxidizing 4-penten-2-yn-1-ol with manganese dioxide in methylene chloride (Non-Patent Literature 3, listed above).

However, manganese dioxide used in the oxidation in Non-Patent Literature 3 causes a large environmental load. Further, the oxidation reaction often involves a danger of explosion. Accordingly, practice of the method in an industrial scale is difficult. A yield is so extremely low as 30%.

The present invention has been made in the aforesaid circumstances, and provides a process for preparing 4-penten-2-ynal, which may be carried out without the danger associated with an oxidation reaction, and in an industrial scale.

As a result of the intensive researches, the present inventors have found that 4-penten-2-ynal may be prepared efficiently and in a short process by hydrolyzing a 5,5-dialkoxy-1-penten-3-yne compound and, thus, have completed the present invention. 4-Penten-2-ynal thus produced is useful as an intermediate for preparing dienynal compounds, such as (9Z)-9,13-tetradecadien-11-ynal.

According to one aspect of the present invention, there is provided a process for preparing 4-penten-2-ynal of the following formula (2):

$$CH_2=CHC\equiv CCHO \qquad (2)$$

the process comprising a step of
hydrolyzing a 5,5-dialkoxy-1-penten-3-yne compound of the following general formula (I):

$$CH_2=CHC\equiv CCH(OR^1)(OR^2) \qquad (1)$$

wherein $R^1$ and $R^2$ represent, independently of each other, a monovalent hydrocarbon group having 1 to 15 carbon atoms, preferably 1 to 8, more preferably 1 to 4, or $R^1$ and $R^2$ may be bonded to each other to form a divalent hydrocarbon group, $R^1$-$R^2$, having from 2 to 10 carbon atoms, to obtain 4-penten-2-ynal (2).

According to the present invention, 4-penten-2-ynal is prepared in a short process and in a high yield. Further, the present process for preparing 4-penten-2-ynal according to the present invention does not involve an oxidation reaction, and therefore, does not involve a danger of explosion.

DETAILED DESCRIPTION OF THE INVENTION

Preparation of 4-Penten-2-Ynal

4-Penten-2-ynal of formula (2) may be produced by hydrolyzing a 5,5-dialkoxy-1-penten-3-yne compound of the following general formula (1) to produce 4-penten-2-ynal (2), as shown in the following chemical reaction formula.

$$CH_2=CHC\equiv CCH(OR^1)(OR^2) \xrightarrow[\text{Water}]{\text{Acid}} CH_2=CHC\equiv CCHO$$
$$(1) \qquad\qquad\qquad (2)$$

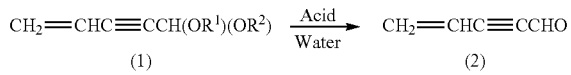

$R^1$ and $R^2$ represent, independently of each other, a monovalent hydrocarbon group having 1 to 15 carbon atoms, preferably 1 to 8, more preferably 1 to 4, or $R^1$ and $R^2$ may be bonded to each other to form a divalent hydrocarbon group, $R^1$-$R^2$, having from 2 to 10 carbon atoms.

Examples of a monovalent hydrocarbon group include linear saturated hydrocarbon groups such as a methyl group, an ethyl group, an n-propyl group, an n-butyl group, an n-pentyl group, an n-hexyl group, an n-heptyl group, an n-octyl group, an n-nonyl group, an n-decyl group, an n-undenyl group, and an n-dodecyl group; branched saturated hydrocarbon groups such as an isopropyl group, a 2-methylpropyl group, and 2-methylbutyl group; linear unsaturated hydrocarbon groups such as a 2-propenyl group; branched unsaturated hydrocarbon groups such as 2-methyl-2-propenyl group; cyclic saturated hydrocarbon groups such as a cyclopropyl group; and their isomers. A part of the hydrogen atoms in these hydrocarbon groups may be substituted with a methyl group or an ethyl group.

A methyl group, an ethyl group, an n-propyl group, and an n-butyl group are preferred in view of handling.

Examples of the divalent hydrocarbon group include linear saturated hydrocarbon groups such as an ethylene group, a 1,3-propylene group, and a 1,4-butylene group; branched saturated hydrocarbon groups such as 1,2-propylene group, a 2,2-dimethyl-1,3-propylene group, a 1,2-butylene group, a 1,3-butylene group, a 2,3-butylene group, and a 2,3-dimethyl-2,3-butylene group; linear unsaturated hydrocarbon groups such as a 1-vinylethylene group; branched unsaturated hydrocarbon groups such as a 2-methyl-1,3-propylene group; cyclic unsaturated hydrocarbon groups such as a 1,2-cyclopropylene group and a 1,2-cyclobutylene group; and their isomers. A part of the hydrogen atoms in these hydrocarbon groups may be substituted with a methyl group or an ethyl group.

In view of the reactivity in elimination of a leaving group, easiness of purification, and availability, the divalent hydrocarbon group is preferably a lower hydrocarbon group, preferably having 2 to 4 carbon atoms. These have high reactivity, and their by-products generated by deprotection are easily removable by water washing or evaporation.

Then, preferred examples of the divalent hydrocarbon group include an ethylene group, a 1,2-propylene group, a 1,3-propylene group, a 1,2-butylene group, a 1,3-butylene group, and a 2,3-dimethyl-2,3-butylene group.

Examples of the 5,5-dialkoxy-1-penten-3-yne compound (1) include 5,5-dimethoxy-1-penten-3-yne, 5,5-diethoxy-1-penten-3-yne, 5,5-dipropoxy-1-penten-3-yne, 5,5-dibutoxy-1-penten-3-yne, 5,5-ethoxymethoxy-1-penten-3-yne, 1-penten-3-yne-1,3-dioxolane, and 1-pentene-3-yne-1,3-dioxane, 5,5-Dimethoxy-1-penten-3-yne, 5,5-diethoxy-1-penten-3-yne, 5,5-dipropoxy-1-penten-3-yne, and 5,5-dibutoxy-1-penten-3-yne are preferred in view of versatility.

The hydrolysis of the 5,5-dialkoxy-1-penten-3-yne compound (1) may be carried out using, for example, an acid or water.

Examples of the acid include inorganic acids such as hydrochloric acid and hydrobromic acid; organic acids such as p-toluenesulfonic acid (p-TsOH), benzenesulfonic acid, trifluoroacetic acid, acetic acid formic acid, oxalic acid; and iodotrimethylsilane and titanium tetrachloride, with p-toluenesulfonic acid and oxalic acid being preferable in view of the reactivity.

The acid may be used either alone or in combination thereof. The acid may be commercially available one.

An amount of the acid is preferably 0.001 to 10.0 mol per mol of the 5,5-dialkoxy-1-penten-3-yne compound (1) in view of the completion of the reaction.

An amount of water is preferably from 18 to 5,000 g per mol of the 5,5-dialkoxy-1-penten-3-yne compound (1) in view of the reactivity.

A solvent may be used in the hydrolysis, if necessary, together with the aforesaid acid or water.

Examples of the solvent include hydrocarbon solvents such as toluene, xylene, hexane, heptane, benzene, and cumene; ether solvents such as tetrahydrofuran, diethyl ether, dibutyl ether, 4-methyltetrahydropyran, cyclopentylmethyl ether, and 1,4-dioxane; polar solvents such as N,N-dimethylformamide, N,N-dimethylacetamide, N-methylpyrrolidone, dimethyl sulfoxide, acetonitrile, acetone, γ-butyrolactone, dichloromethane and chloroform; and alcohols such as methanol and ethanol.

The solvent may be used either alone or in combination thereof. The solvent may be commercially available one.

An optimum solvent varies, depending on an acid used. For instance, when p-toluenesulfonic acid is used as the acid, the solvent is preferably tetrahydrofuran in view of the reactivity.

An amount of the solvent is preferably from 0 to 3,000 g per mol of the 5,5-dialkoxy-1-penten-3-yne compound (1) in view of the reactivity.

An antioxidant may be used if necessary, together with the aforesaid acid or water in the hydrolysis.

Examples of the antioxidant include dibutylhydroxyltoluene (BHT), vitamin A, vitamin C, vitamin E, uric acid, glutathione, and meladonin.

An amount of the antioxidant is preferably from 0.001 to 1,000 g per mol of the 5,5-dialkoxy-1-penten-3-yne compound (1) in view of the yield.

The antioxidant may be used either alone or in combination thereof. The antioxidant may be commercially available one.

A reaction temperature in the hydrolysis varies, depending on an acid or solvent used, and is preferably from 5 to 180° C. in view of the reactivity.

A reaction time in the hydrolysis varies, depending on a solvent used or a production scale, and is preferably from 0.5 to 55 hours in view of the reactivity.

Preparation of 5,5-dialkoxy-1-penten-3-yne compound (1)

The 5,5-dialkoxy-1-penten-3-yne compound (1) may be synthesized, for example, by eliminating a leaving group Z at position 5 of a 2-ynal acetal compound of the following general formula (3) in the presence of a base, as shown in the following chemical reaction formula.

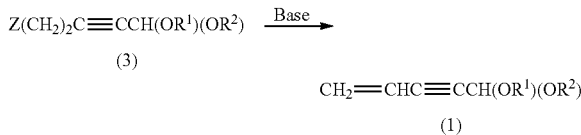

$R^1$ and $R^2$ in the 2-ynal acetal compound (3) represent, independently of each other, a monovalent hydrocarbon group having 1 to 15 carbon atoms, preferably 1 to 8, more preferably 1 to 4, or $R^1$ and $R^2$ may be bonded to each other to form a divalent hydrocarbon group, $R^1$-$R^2$, having from 2 to 10 carbon atoms.

Where $R^1$ and $R^2$ in the 2-ynal acetal compound (3) are a monovalent hydrocarbon group or a divalent hydrocarbon group, $R^1$ and $R^2$ may be selected from the options for $R^1$ and $R^2$ in the 5,5-dialkoxy-1-penten-3-yne compound (1).

Z in the 2-ynal acetal compound (3) represents a leaving group and is an alkoxy group having 1 to 12 carbon atoms, an acyloxy group having 1 to 10 carbon atoms, a silyloxy group having 3 to 20 carbon atoms, an alkanesulfonylxoy group having 1 to 10 carbon atoms, an arenesulfonyloxy group having 6 to 20 carbon atoms, or a halogen atom.

The number of the carbon atoms of the alkoxy group is 1 to 12, preferably 1 to 9.

Examples of the alkoxy group include linear saturated alkoxy groups such as a methoxy group, an ethoxy group, an n-propoxy group, an n-butoxy group, and an n-pentyloxy group; branched saturated alkoxy groups such as an isopropoxy group and a t-butoxy group; linear unsaturated alkoxy groups such as a 2-propenyloxy group and a 2-propynyloxy group; branched unsaturated alkoxy groups such as a 2-methyl-2-propenyloxy group; cyclic alkoxy groups such as a cyclopropyloxy group, a 2-methylcyclopropyloxy group, a cyclobutyloxy group, and a cyclopentyloxy group; alkoxy groups comprising an aromatic ring such as a benzyloxy group and a p-methoxybenzyloxy group; alkoxyalkoxy groups such as a methoxymethoxy group, a methoxyethoxy group, a 2-methoxyethoxymethoxy group, a benzyloxymethoxy group, a p-methoxybenzyloxymethoxy group, a 1-ethoxyethoxy group, and a tetrahydropyran-2-yloxy group; and halogenated alkoxy groups such as a 2,2,2-trichloroethoxy group and a pentafluoroethoxy group; and their isomers. A part of the hydrogen atoms in these alkoxy groups may be substituted with a methyl group or an ethyl group.

Particularly preferable examples of the alkoxy group include a methoxy group, an ethoxy group, a 2-propenyloxy group, a methoxymethoxy group, a methoxyethoxy group, and a 1-ethoxyethoxy group because of their availability, and because by-products formed in the deprotection are easily removed by water washing or evaporation.

The number of the carbon atoms of the acyloxy group is 1 to 10, preferably 1 to 7.

Examples of the acyloxy group include linear aliphatic acyloxy groups such as a formyloxy group, an acetoxy group, a propanoyloxy group, a butanoyloxy group, and a crotonyloxy group; branched alphatic acyloxy groups such as a 2-methylpropanoyloxy group and a pivaloyloxy group; halogenated acyloxy groups such as a trichloroacetoxy group and a trifluoroacetoxy group; and aromatic acyloxy groups such as a benzoyloxy group; and their isomers. A part of the hydrogen atoms in these acyloxy groups may be substituted with a methyl group or an ethyl group.

Particularly preferable examples of the acyloxy group include an acetoxy group, a propanoyloxy group, a pivaloyloxy group, a benzoyloxy group in view of the availability.

The number of the carbon atoms of the silyloxy group is 3 to 20, preferably 3 to 16, more preferably 3 to 10.

Examples of the silyloxy group include trialkylsilyloxy groups such as trimethylsilyloxy group, a triethylsilyloxy group, a triisopropylsilyloxy group, and a t-butyldimethylsilyloxy group; and monoalkyldiarylsilyloxy groups such as a t-butyldiphenylsilyloxy group; and their isomers. A part of their hydrogen atoms in these silyloxy groups may be substituted with a methyl group or an ethyl group.

Particularly preferable examples of the silyloxy group include a trimethylsilyloxy group, a triethylsilyloxy group in view of the availability, and in view of the fact that by-products generated by deprotection can be easily removed by washing or concentration.

The number of the carbon atoms of the alkanesulfonyloxy group is 1 to 10, preferably 1 to 7.

Examples of the alkanesulfonyloxy group include a methanesulfonyloxy group, an ethanesulfonyloxy group, a 1-butanesulfonyloxy group, a 1-octanesulfonyloxy group, an allylsulfonyloxy group, a 10-camphorsulfonyloxy group, a trifluoromethanesulfonyloxy group, and a benzylsulfonyloxy group; and their isomers. A part of the hydrogen atoms in these alkanesulfonyloxy groups may be substituted with a methyl group or an ethyl group.

Particularly preferable examples of the alkanesulfonyloxy group include a methanesulfonyloxy group and an ethanesulfonyloxy group in view of the availability.

The number of the carbon atoms of the arenesulfonyloxy group is 6 to 20, preferably 6 to 15, more preferably 6 to 7.

Examples of the arenesulfonyloxy group include a benzenesulfonyloxy group, a 4-chlorobenzenesulfonyloxy group, a 4-methoxybenzenesulfonyloxy group, a 2-nitrobenzenesulfonyloxy group, a 2,4,6-trimethylbenzenesulfonyloxy group, a p-toluenesulfonyloxy group, a 1-naphthalenesulfonyloxy group, and a 2-naphthalenesulfonyloxy group; and their isomers. A part of the hydrogen atoms in these arenesulfonyloxy groups may be substituted with a methyl group or an ethyl group.

Particularly preferred examples of the arenesulfonyloxy group include a benzenesulfonyloxy group and a p-toluenesulfonyloxy group in view of the availability.

Examples of the halogen atoms include a fluorine atom, a chlorine atom, a bromine atom and an iodine atom.

Particularly preferred examples of the halogen atoms are a chlorine atom and a bromine atom in view of the availability.

Specific examples of the 2-ynal acetal compound (3) with Z being an alkoxy group having 1 to 12 carbon atoms include a 1,1-dialkoxy-5-(methoxymethoxy)-2-pentyne compound such as 1,1-dimethoxy-5-(methoxymethoxy)-2-pentyne and 1,1-diethoxy-5-(methoxymethoxy)-2-pentyne; a 1,1-dialkoxy-5-(methoxyethoxy)-2-pentyne compound such as 1,1-dimethoxy-5-(methoxyethoxy)-2-pentyne, 1,1-diethoxy-5-(methoxyethoxy)-2-pentyne; a 1,1-dialkoxy-5-methoxy-2-pentyne compound such as 1,1-dimethoxy-5-methoxy-2-pentyne and 1,1-diethoxy-5-methoxy-2-pentyne; and a 1,1-dialkoxy-5-ethoxy-2-pentyne compound such as 1,1-dimethoxy-5-ethoxy-2-pentyne and 1,1-diethoxy-5-ethoxy-2-pentyne.

Specific examples of the 2-ynal acetal compound (3) with Z being an acyloxy group having 1 to 10 carbon atoms include a 1,1-dialkoxy-5-acetyloxy-2-pentyne compound such as 1,1-dimethoxy-5-acetyloxy-2-pentyne and 1,1-diethoxy-5-acetyloxy-2-pentyne.

Specific examples of the 2-ynal acetal compound (3) with Z being a silyloxy group having 3 to 20 carbon atoms include a 1,1-dialkoxy-5-trimethylsilyloxy-2-pentyne compound such as 1,1-dimethoxy-5-trimethylsilyloxy-2-pentyne and 1,1-diethoxy-5-trimethylsilyloxy-2-pentyne; a 1,1-dialkoxy-5-triethylsilyloxy-2-pentyne compound such as 1,1-dimethoxy-5-triethylsilyloxy-2-pentyne and 1,1-diethoxy-5-triethylsilyloxy-2-pentyne.

Specific examples of the 2-ynal acetal compound (3) with Z being an alkanesulfonyloxy group having 1 to 10 carbon atoms include a 1,1-dialkoxy-5-methanesulfonyloxy-2-pentyne compound such as 1,1-dimethoxy-5-methanesulfonyloxy-2-pentyne, and 1,1-diethoxy-5-methanesulfonyloxy-2-pentyne.

Specific examples of the 2-ynal acetal compound (3) with Z being an arenesulfonyloxy group having 6 to 20 carbon atoms include a 1,1-dialkoxy-5-(p-toluenesulfonyloxy)-2-pentyne compound such as 1,1-dimethyl-5-(p-toluenesulfonyloxy)-2-pentyne and 1,1-diethoxy-5-(p-toluenesulfonyloxy)-2-pentyne.

Specific examples of the 2-ynal acetal compound (3) with Z being a halogen atom include a 1,1-dialkoxy-5-chloro-2-pentyne compound such as 1,1-dimethoxy-5-chloro-2-pentyne and 1,1-diethoxy-5-chloro-2-pentyne; and 1,1-dialkoxy-5-bromo-2-pentyne compound such as 1,1-dimethoxy-5-bromo-2-pentyne and 1,1-diethoxy-5-bromo-2-pentyne.

An acidity at position 4 in the 2-ynal acetal compound (3) is highly increased by the electronic effects of the acetal group and the triple bond, so that an elimination reaction of the leaving group Z may take place, even when the leaving group Z is an alkoxy, acyloxy or silyloxy group which has a low leaving ability, without need to convert the leaving group into another leaving group having a high leaving ability, and, as a matter of course, also when the leaving group Z is an alkanesulfonyloxy group, an arenesulfonyloxy group or a halogen atom which all have a high leaving ability.

In a case where the leaving Z is an alkoxy group, an acyloxy group, or a silyloxy group which has a low leaving ability, the 2-ynal acetal compound (3) advantageously has a high thermal stability, compared to an alkanesulfonyloxy group, an arenesulfonyloxy group and a halogen atom. This allows purification by distillation, which is industrially advantageous.

Meanwhile, an acidity at position 4 is not high in a compound having a hydrocarbon group instead of the acetal group, so that an elimination reaction does not proceed efficiently, particularly in a case of a leaving group which has a low elimination ability, i.e., an alkoxy group, an acyloxy group or a silyloxy group.

Examples of the base to be used in the elimination reaction of the leaving group Z include hydroxides such as sodium hydroxide, potassium hydroxide, calcium hydroxide and magnesium hydroxide; metal alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic reagents such as methyllithium, ethyllithium, n-butyllithium, methylmagnesium chloride, sodium dimsyl, sodium acetylide, and potassium acetylide; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydrides such as sodium hydride, potassium hydride, and calcium hydride; and amines such as triethylamine, piperidine, pyrrolidine, pyridine, 4-dimethylaminopyridine, and 1,8-diazabicyclo[5.4.0]-7-undecene (DBU).

Preferably examples of the base include metal alkoxides such as sodium methoxide, sodium ethoxide, and potassium t-butoxide in view of suppressing the formation of allene compounds and impurities so as to obtain the 4-penten-2-ynal (2) in a high yield.

The base may be used either alone or in combination thereof. The base may be commercially available one.

An amount of the base is preferably for 0.6 to 3.0 mol, more preferably from 0.7 to 2.0 mol, and even more preferably from 0.8 to 1.5 mol, per mol of the 2-ynal acetal compound (3).

A solvent may be used in the elimination reaction, if necessary.

Examples of the solvent include ethers such as diethyl ether, dibutyl ether, tetrahydrofuran (THF), 4-methyltetrahydropyran, cyclopentyl methyl ether, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide (DMF), N,N-dimethylacetamide, N-methylpyrrolidone, dimethyl sulfoxide, γ-butyrolactone, 1,3-dimethyl-2-imidazolidinone, and hexamethylphosphoric triamide; nitriles such as acetonitrile and propionitrile; esters such as ethyl acetate and n-butyl acetate; and alcohols such as methanol, ethanol, and t-butyl alcohol.

The solvent may be used either alone or in combination thereof. The solvent may be commercially available one.

An amount of the solvent is preferably from 0 to 10,000 g, more preferably from 0 to 5,000 g per mol of the 2-ynal acetal compound (3).

When the base is a metal alkoxide, organometallic reagent, metal amide, or metal hydride, a temperature of the elimination reaction is preferably from −78 to 70° C., more preferably from −50 to 40° C., and even more preferably −30 to 30° C., in view of the yield.

When the base is an amine, the temperature of the elimination reaction is preferably from 0 to 180° C., more preferably from 10 to 150° C., and even more preferably from 20 to 130° C., in view of the yield.

A reaction time of the elimination may vary, depending on a solvent or a production scale, and is preferably from 0.5 to 55 hours in view of the reactivity.

Preparation of (9Z)-9,13-tetradecadien-11-ynal

The aforesaid process for preparing 4-penten-2-ynal may be useful for preparing, for instance, 9,13-tetradecadien-11-ynal such as (9Z)-9,13-tetradecadien-11-ynal which is a pheromone of Avocado seed moth (*Stenoma catenifer*) which is known as a most serious pest against avocado.

9,13-Tetradecadien-11-ynal of the following formula (6) may be produced by a Wittig reaction of the aforesaid 4-penten-2-ynal (2) with a triarylphosphonium 9,9-dialkoxynonylide compound of the following general formula (4) to obtain a 14,14-dialkoxy-1,5-tetradecadien-3-yne compound of the following general formula (5); and hydrolysis of the 14,14-dialkoxy-1,5-tetradecadien-3-yne compound (5), as shown in the following chemical reaction formula.

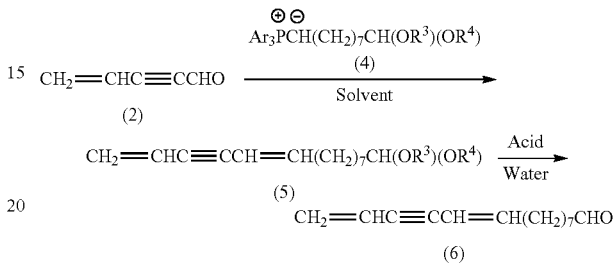

First, the Wittig reaction will be explained below.
The triarylphosphonium 9,9-dialkoxynonylide compound is represented by the following general formula (4).

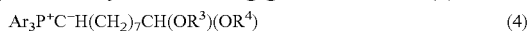

wherein $R^3$ and $R^4$ represent, independently of each other, a monovalent hydrocarbon group having 1 to 15 carbon atoms, preferably 1 to 8, more preferably 1 to 4, or $R^3$ and $R^4$ may be bonded to each other to form a divalent hydrocarbon group, $R^3$-$R^4$, having from 2 to 10 carbon atoms.

Examples of $R^3$ and $R^4$ are same as the examples of $R^1$ and $R^2$ in the 5,5-dialkoxy-1-penten-3-yne compound (1).

Ar in the triarylphosphonium 9,9-dialkoxynonylide compound (4) may be same with or different from each other and represent an aryl group. The number of the carbon atoms of the aryl group is preferably 6 to 24, more preferably 6 to 12, and even more preferably 6 or 7.

Examples of the aryl group include a phenyl group (Ph group), a tolyl group, a naphtyl group and an anthracenyl group, with a phenyl group being preferable in view of easiness of the synthesis. It is preferred that all of the three aryl groups are a phenyl group in view of easiness of the synthesis.

Example of the triarylphosphonium 9,9-dialkoxynonylide compound (4) include a triphenylphosphonium 9,9-dialkoxynonylide compound such as triphenylphosphonium 9,9-dimethoxynonylide, triphenylphosphonium, 9,9-diethoxynonylide, triphenylphosphonium 9,9-dipropoxynonylide, and triphenylphosphonium 9,9-dibutyoxynonylide; and tritolylphosphonium 9,9-dialkoxynonylide compound such as tritolylphosphonium 9,9-dimethoxynonylide, tritolylphosphonium 9,9-diethoxynonylide, tritolylphosphonium 9,9-dipropioxynonylide, and tritolylphosphonium 9,9-dibutoxynonylide.

The triarylphosphonium 9,9-dialkoxynonylide compound (4) may be used either alone or in combination thereof. The triarylphosphonium 9,9-dialkoxynonylide compound (4) may be commercially available one or may be synthesized in house.

The triarylphosphonium 9,9-dialkoxynonylide compound (4) may be produced by reacting a 9-halo-1,1-dialkoxynonane compound of the following general formula (7) with a phosphorus compound of the following general formula (8) to obtain a 9,9-dialkoxynonyltriarylphosphonium halide compound of the following general formula (9); and subjecting the 9,9-dialkoxynonyltriarylphosphonium halide compound (9) thus obtained to deprotonation in the presence of a base to obtain the triarylphosphonium 9,9-dialkoxynonylide compound (4), as shown in the following chemical reaction formula.

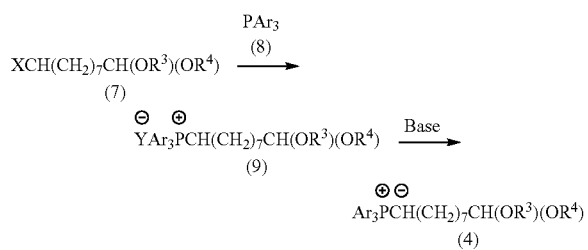

$R^3$ and $R^4$ in the 9-halo-1,1-dialkoxynonane compounds (7) represent, independently of each other, a monovalent hydrocarbon group having 1 to 15 carbon atoms, preferably 1 to 8, more preferably 1 to 4, or $R^3$ and $R^4$ may be bonded to each other to form a divalent hydrocarbon group, $R^3$-$R^4$, having from 2 to 10 carbon atoms.

Examples of $R^3$ and $R^4$ are same as the examples of the $R^1$ and $R^2$ in the 5,5-dialkoxy-1-penten-3-yne compound (1).

X in the 9-halo-1,1-dialkoxynonane compounds (7) represents a halogen atom, such as a chlorine atom, a bromine atom, and an iodine atom, with a chloride atom and a bromine atom being preferable in view of versatility.

Example of the 9-halo-1,1-dialkoxynonane compounds (7) include a 9-chloro-1,1-dialkoxynonane compound such as 9-chloro-1,1-dimethoxynonane, 9-chloro-1,1-diethoxynonane, 9-chloro-1,1-dipropoxynonane, 9-chloro-1,1-dibutoxynonane, 9-chloro-1,1-dipentoxynonane, 9-chloro-1,1-dihexoxynonane, 9-chloro-1,1-diheptoxynonane, and 9-chloro-1,1-dioctoxynonane; a 9-bromo-1,1-dialkoxynonane compound such as 9-bromo-1,1-dimethoxynonane, 9-bromo-1,1-diethoxynonane, 9-bromo-1,1-dipropoxynonane, 9-bromo-1,1-dibutoxynonane, 9-bromo-1,1-dipentoxynonane, 9-bromo-1,1-dihexoxynonane, 9-bromo-1,1-diheptoxynonane, 9-bromo-1,1-dioctoxynonane; and a 9-iodo-1,1-dihexoxynonane compound such as 9-iodo-1,1-dimethoxynonane, 9-iodo-1,1-diethoxynonane, 9-iodo-1,1-dipropoxynonane, 9-iodo-1,1-dibutoxynonane, 9-iodo-1,1-dipentoxynonane, 9-iodo-1,1-dihexoxynonane, 9-iodo-1,1-diheptoxynonane and 9-iodo-1,1-dioctoxynone.

Ar in the phosphorus compound (8) may be same with or different from each other and represent an aryl group. The number of the carbon atoms of the aryl group is preferably 6 to 24, more preferably 6 to 12, and even more preferably 6 or 7.

Examples of the aryl group include a phenyl group (Ph group), a tolyl group, a naphtyl group and an anthracenyl group, with a phenyl group being preferable in view of easiness of the synthesis. It is more preferred that all of the three aryl groups are a phenyl group in view of easiness of the synthesis.

Examples of the phosphorus compound (8) include a triarylphosphine compound such as triphenylphosphine and tritolylphosphine, with triphenylphosphine being preferable in view of the reactivity.

An amount of the phosphorus compound (8) is preferably from 0.8 to 5.0 mol per mol of the 9-halo-1,1-dialkoxynonane compounds (7) in view of the reactivity.

A halide may be used, if necessary, in the preparation of the 9,9-dialkoxynonyltriarylphosphonium halide compound (9).

Examples of the halide include sodium iodide, potassium iodide, sodium bromide, and potassium bromide, with iodide such as sodium iodide and potassium iodide being preferable in view of the reactivity.

The halide may be used either alone or in combination thereof. The halide may be commercially available one.

An amount of the halide is preferably from 0.1 to 5.0 mol per mol of the 9-halo-1,1-dialkoxynonane compounds (7) in view of the reactivity.

A base may be added, if necessary, in the preparation of the 9,9-dialkoxynonyltriarylphosphonium halide compound (9).

Examples of the base include alkali metal carbonates such as potassium carbonate and sodium carbonate; alkaline earth metal carbonates such as calcium carbonate and magnesium carbonate; and amines such as triethylamine, tripropylamine, triisopropylamine, tributylamine, N,N-diethylaniline, and pyridine, with alkali metal carbonates being preferable in viewing of handling.

The base may be used either alone or in combination thereof. The base may be commercially available one.

An amount of the base is preferably from 0.001 to 1.0 mol per mol of the 9-halo-1,1-dialkoxynonane compounds (7) in view of the reactivity.

An optimum temperature for the preparation of the 9,9-dialkoxynonyltriarylphosphonium halide compound (9) varies, depending on a solvent used, and is preferably from 60 to 180° C. in view of the reactivity.

A reaction time in the preparation of the 9,9-dialkoxynonyltriarylphosphonium halide compound (9) varies, depending on a solvent used and a production scale, and is preferably from 3 to 55 hours.

$R^3$ and $R^4$ in the 9,9-dialkoxynonyltriarylphosphonium halide compound (9) represent, independently of each other, a monovalent hydrocarbon group having 1 to 15 carbon atoms, preferably 1 to 8, more preferably 1 to 4, $R^3$ and $R^4$ may be bonded to each other to form a divalent hydrocarbon group, $R^3$-$R^4$, having from 2 to 10 carbon atoms.

Examples of $R^3$ and $R^4$ are same as the examples of $R^1$ and $R^2$ in the 5,5-dialkoxy-1-penten-3-yne compound (1).

Y in the 9,9-dialkoxynonyltriarylphosphonium halide compound (9) represents a halogen atom, and examples thereof include a chlorine atom, a bromine atom, and an iodine atom.

In a case where a halide is not used in the preparation of the 9,9-dialkoxynonyltriarylphosphonium halide compound (9), Y is the halogen atom same as X. In a case where iodide is used as a halide, Y is the halogen atom same as X or an iodine atom.

Ar in the 9,9-dialkoxynonyltriarylphosphonium halide compound (9) represents an aryl group. Ar is as defined for the phosphorus compound (8).

Example of the 9,9-dialkoxynonyltriarylphosphonium halide compound (9) include a 9,9-dialkoxynonyltriarylphosphonium chloride compound such as 9,9-dimethoxynonyltriphenylphosphonium chloride, 9,9-diethoxynonyltriphenylphosphonium chloride, 9,9-dipropoxynonyltriphenylphosphonium chloride, and 9,9-butoxynonyltriphenylphosphonium chloride; a 9,9-dialkoxynonyltriphenylphosphonium bromide compound such as 9,9-dimethoxynonyltriphenylphosphonium bromide, 9,9-diethoxynonyltriphenylphosphonium bromide, 9,9-dipropoxynonyltriphenylphosphonium bromide, and 9,9-dibutoxynonyltriphenylphosphonium bromide; a 9,9-dialkoxynonyltriphenylphosphonium iodide compound such as 9,9-dimethoxynonyltriphenylphosphonium iodide, 9,9-diethoxynonyltriphenylphosphonium iodide, 9,9-dipropoxynonyltriphenylphosphonium iodide, and 9,9-dibutoxynonyltriphenylphosphonium iodide; a 9,9-dialkoxynonyltritolylphosphonium chloride compound such as 9,9-dimethoxynonyltritolylphosphonium chloride, 9,9-diethoxynonyltritolylphosphonium chloride, 9,9-dipropoxynonyltritolylphosphonium chloride, and 9,9-dibutoxynonyltritolylphosphonium chloride; a 9,9-dialkoxynonyltritolylphosphonium bromide compound such as 9,9-dimethoxynonyltritolylphosphonium bromide, 9,9-diethoxynonyltritolylphosphonium bromide, 9,9-dipropoxynonyltritolylphosphonium bromide, and 9,9-dibutoxynonyltritolylphosphonium bromide; and a 9,9-dialkoxynonyltritolylphosphonium iodide compound such as 9,9-dimethoxynonyltyritolylphosphonium iodide, 9,9-diethoxynonyltritolylphosphonium iodide; 9,9-dipropoxynonyltritolylphosphonium iodide, and 9,9-dibutoxynonyltritolylphosphonium iodide.

The triarylphosphonium 9,9-dialkoxynonylide compound (4) is obtained by subjecting the 9,9-dialkoxynonyltriarylphosphonium halide compound (9) thus obtained to deprotonation in the presence of a base.

The triarylphosphonium 9,9-dialkoxynonylide compound (4) may be prepared by adding a base directly in the reaction system after the preparation of the 9,9-dialkoxynonyltriarylphosphonium halide compound (9). Alternatively, the 9,9-dialkoxynonyltriarylphosphonium halide compound (9) is isolated and purified, to which a base is then added to obtain the triarylphosphonium 9,9-dialkoxynonylide compound (4).

Examples of the base to be used in the preparation of the triarylphosphonium 9,9-dialkoxynonylide compound (4) include alkyllithium such as n-butyllithium and tert-butyllithium; metal alkoxides such as potassium tert-butoxide, sodium tert-butoxide, potassium methoxide, sodium methoxide, potassium ethoxide, sodium ethoxide, and metal amides such as lithium diisopropylamide and sodium bis(trimethylsilyl)amide. Metal alkoxides are preferable, particularly potassium tert-butoxide, sodium methoxide, and sodium ethoxide, in view of the reactivity.

An amount of the base is preferably from 0.7 to 5.0 mol per mol of the 9-halo-1,1-dialkoxynonane compounds (7) in view of the reactivity.

A temperature in the preparation of the triarylphosphonium 9,9-dialkoxynonylide compound (4) varies, depending on the solvent and the base, and is preferably from −78 to 25° C.

A reaction time in the preparation of the triarylphosphonium 9,9-dialkoxynonylide compound (4) varies, depending on the solvent and the production scale, and is preferably from 0.5 to 50 hours.

A solvent may be used, if necessary, in the preparation of the 9,9-dialkoxynonyltriarylphosphonium halide compound (9) and in the preparation of the triarylphosphonium 9,9-dialkoxynonylide compound (4).

Examples of the solvent include ether solvents such as tetrahydrofuran, diethyl ether, dibutyl ether, 4-methyltetrahydropyran, cyclopentyl methyl ether; and 1,4-dioxane; hydrocarbon solvents such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, and chloroform, with the ether solvents such as tetrahydrofuran and the polar solvents such as acetonitrile and N,N-dimethylacetamide being preferable in view of the reactivity.

The solvent may be used either alone or in combination thereof. The solvent may be commercially available one.

An amount of the solvent is preferably from 50 to 5,000 g per mol of the 9-halo-1,1-dialkoxynonane compounds (7) or the 9,9-dialkoxynonyltriaylphosphonium halide compound (9) in view of the reactivity.

An amount of the triarylphosphonium 9,9-dialkoxynonylide compound (4) is preferably from 1.0 to 4.0 mol, more preferably from 1.0 to 2.0 mol, per mol of 4-penten-2-ynal (2) in view of the reactivity.

A solvent may be used in a Wittig reaction, if necessary.

Examples of the solvent include ether solvents such as tetrahydrofuran, diethyl ether, dibutyl ether, 4-methyltetrahydropyran, cyclopentyl methyl ether, and 1,4-dioxane, hydrocarbon solvents such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, and chloroform. Ether solvents such as tetrahydrofuran and polar solvents such as acetonitrile, N,N-dimethylformamide, and N,N-dimethylacetamide are preferred in view of the reactivity.

The solvent may be used either alone or in combination thereof. The solvent may be commercially available one.

An amount of the solvent is preferably from 50 to 5000 g per mol of 4-penten-2-ynal (3) in view of the reactivity.

An optimum temperature in a Wittig reaction varies, depending on the solvent used, and is preferably from −78 to 40° C. In a case where a Wittig reaction is carried out in preference to Z, the temperature is preferably −78 to 10° C. In a case where a Wittig reaction is carried out in preference to E, the temperature is preferably −78 to −40° C. Then, an intermediate product is allowed to react in a modified Schlosser condition where the intermediate product is treated with a strong base such as phenyl lithium.

A reaction time in the Wittig reaction varies, depending on a production scale, and is preferably from more than 0 (>0) to 50 hours.

Geometric isomers of the 14,14-dialkoxy-1,5-tetradecadien-3-yne compound (5) are a 14,14-dialkoxy-(5Z)-1,5-tetradecadien-3-yne compound of the following general formula (5-Z), a 14,14-dialkoxy-(5E)-1,5-tetradecadien-3-yne compound of the following general formula (5-E), and mixtures thereof.

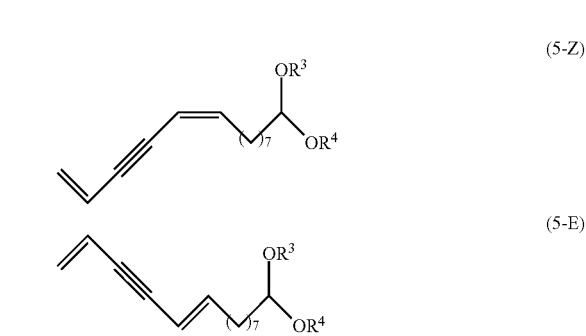

Example of 14,14-dialkoxy-1,5-tetradecadien-3-yne compound (5) include a 14,14-dialkoxy-(5Z)-1,5-tetradecadien-3-yne compound such as 14,14-dimethoxy-(5Z)-1,5-tetradecadien-3-yne, 14,14-diethoxy-(5Z)-1,5-tetradecadien-3- yne, 14,14-dipropoxy-(5Z)-1,5-tetradecadien-3-yne, 14,14-dibutoxy-(5Z)-1,5-tetradecadien-3-yne, 14,14-dipentoxy-(5Z)-1,5-tetradecadien-3-yne, 14,14-dihexoxy-(5Z)-1,5-tetradecadien-3-yne, 14,14-diheptoxy-(5Z)-1,5-tetradecadien-3-yne, and 14,14-dioctoxy-(5Z)-1,5-tetradecadien-3-yne, and a 14,14-dialkoxy-(5E)-1,5-tetradecadien-3-yne compound such as 14,14-dimethoxy-(5E)-1,5-tetradecadien-3-yne, 14,14-diethoxy-(5E)-1,5-tetradecadien-3-yne, 14,14-dipropoxy-(5E)-1,5-tetradecadien-3-yne, 14,14-dibutoxy-(5E)-1,5-tetradecadien-3-yne, 14,14-dipentoxy-(5E)-1,5-tetradecadien-3-yne, 14,14-dihexoxy-(5E)-1,5-tetradecadien-3-yne, 14,14-diheptoxy-(5E)-1,5-tetradecadien-3-yne, and 14,14-dioctoxy-(5E)-1,5-tetradecadien-3-yne.

Next, the hydrolysis step will be explained.

In the hydrolysis, the 14,14-dialkoxy-1,5-tetradecadien-3-yne compound (5) may be used either alone or in combination thereof.

For instance, a mixture of the 14,14-dialkoxy-(5Z)-1,5-tetradecadien-3-yne compound and the 14,14-dialkoxy-(5E)-1,5-tetradecadien-3-yne compound may be used to obtain a mixture of (9Z)-9,13-tetradecadien-11-ynal and (9E)-9,13-tetradecadien-11-ynal.

The hydrolysis may be carried out using, for example, an acid or water.

Examples of the acid include inorganic acids such as hydrochloric acid and hydrobromic acid, p-toluenesulfonic acid, benzenesulfonic acid, trifluoroacetic acid, acetic acid, formic acid, oxalic acid, iodotrimethylsilane, and titanium tetrachloride, with acetic acid, formic acid, and oxalic acid being preferable in view of the reactivity.

The acid may be used either alone or in combination thereof. The acids may be commercially available one.

An amount of the acid is preferably 0.01 to 10.0 mol per mol of the 14,14-dialkoxy-1,5-tetradecadien-3-yne compound (5).

An amount of water is preferably from 18 to 3,000 g per mol of the 14,14-dialkoxy-1,5-tetradecadien-3-yne compound (5).

A solvent may be used in the hydrolysis, if necessary, together with the aforesaid acid or water.

Examples of the solvent include hydrocarbon solvents such as toluene, xylene, hexane, heptane, benzene, and cumene; ether solvents such as tetrahydrofuran, diethyl ether, dibutyl ether, 4-methyltetrahydropyran, cyclopentylmethyl ether, and 1,4-dioxane; polar solvents such as N,N-dimethylformamide, N,N-dimethylacetamide, N-methylpyrrolidone, dimethyl sulfoxide, acetonitrile, acetone, γ-butyrolactone, dichloromethane and chloroform; and alcohols such as methanol and ethanol.

The solvent may be used either alone or in combination thereof. The solvent may be commercially available one.

An optimum solvent varies, depending on an acid used. For instance, when oxalic acid is used as the acid, the solvent is preferably tetrahydrofuran, acetone, and γ-butyrolactone in view of the reactivity.

An amount of the solvent is preferably from 0 to 3,000 g per mol of the 14,14-dialkoxy-1,5-tetradecadien-3-yne compound (5) in view of the reactivity.

A temperature in the hydrolysis varies, depending on an acid or solvent used, and is preferably from 5 to 180° C. in view of the reactivity.

A reaction time in the hydrolysis varies, depending on an acid or solvent used or a production scale, and is preferably from 1 to 55 hours in view of the reactivity.

Examples of the 9,13-tetradecadien-11-ynal (6) include (9Z)-9,13-tetradecadien-11-ynal of the following formula (6-Z), (9E)-9,13-tetradecadien-11-ynal of the following formula (6-E), and mixtures thereof.

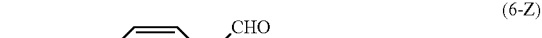

(6-Z)

(6-E)

EXAMPLES

The present invention will be further described with reference to the following Examples. It should be understood that the present invention is not limited to or by the Examples.

The term "purity" as used herein means an area percentage in gas chromatography (GC), unless otherwise specified. The term "production ratio" means a ratio of area percentages in GC. The yield is calculated from the area percentages in GC.

In the Examples, monitoring of the reactions was carried out in the following GC conditions.

GC conditions: Capillary gas chromatograph GC-2014, ex Shimadzu Corporation; column: DB-5; 0.25 mm×0.25 mmϕ×30 m; carrier gas: He (1.55 mL/min); detector: FID; column temperature: 150° C., elevated by 5° C./min, up to 230° C.

The yield was calculated according to the following equation in consideration of purities (% GC) of a starting material and a product.

Yield (%)={[(weight of a product obtained by a reaction×% GC)/molecular weight of a product]÷[(weight of a starting material in a reaction×% GC)/molecular weight of a starting material]}×100

Example 1

Preparation of 5,5-diethoxy-1-penten-3-yne (1: $R^1$=Et, $R^2$=Et)

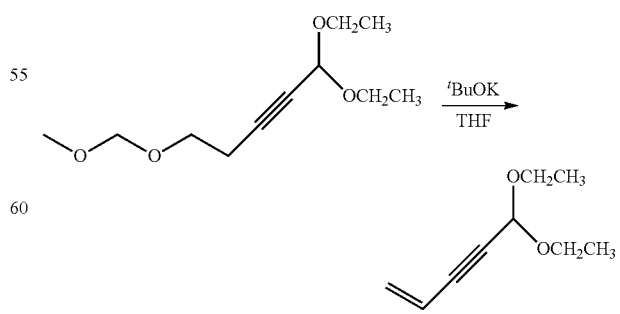

Potassium t-butoxide (tBuOK) (402.39 g, 3.59 mol) and tetrahydrofuran (THF) (1856.64 g) were placed in a reactor at room temperature and stirred at 10 to 15° C. for 28 minutes. Then, 1,1-diethoxy-5-(methoxymethoxy)-2-pentyne (3: $R^1$=Et, $R^2$=Et; Z=$CH_3OCH_2O$) (704.18 g, 3.26 mol, purity: 100%) was added dropwise to the reactor at 10 to 15° C. After the completion of the dropwise addition, the reaction mixture was stirred at 10 to 20° C. for 5.5 hours. Next, water (1953.60 g) was added to the reaction mixture, followed by phase separation and removal of the aqueous phase to obtain the organic phase. Then, the organic phase was concentrated at a reduced pressure and the residue was subjected to distillation at a reduced pressure (51.3 to 57.9° C./3.0 mmHg (0.40 kPa)) to obtain 5,5-diethoxy-1-penten-3-yne (1: $R^1$=Et, $R^2$=Et) (436.26 g, 2.78 mol, purity: 98.41%) in a yield of 85.52%.

The following is the spectrum data of 5,5-diethoxy-1-penten-3-yne (1: $R^1$=Et, $R^2$=Et) thus produced.

[Nuclear magnetic resonance spectrum] $^1$H-NMR (500 MHz, $CDCl_3$): δ 1.22 (6H, t, 7.1 Hz), 3.58 (2H, dq, J=6.9 Hz, 7.8 Hz), 3.73 (2H, dq, J=6.9 Hz, 7.9 Hz), 5.36 (1H, d, J=1.6 Hz), 5.52 (1H, dd, J=11.0 Hz, 2.3 Hz), 5.69 (1H, dd, J=17.6 Hz, 2.3 Hz), 5.81 (1H, ddd, J=17.8 Hz, 10.9 Hz, 1.5 Hz); $^{13}$C-NMR (125 MHz, $CDCl_3$): δ 15.01, 60.81, 83.76, 84.89, 91.57, 116.04, 128.48.

[Mass spectrum] EI-Mass spectrum (70 eV): m/z 153 ($M^+$–1), 125, 109, 81, 63, 53.

[Infrared absorption spectrum] (NaCl): νmax 2977, 2886, 1355, 1328, 1162, 1091, 1054, 1012.

Example 2

Preparation of 5,5-diethoxy-1-penten-3-yne (1: $R^1$=Et, $R^2$=Et)

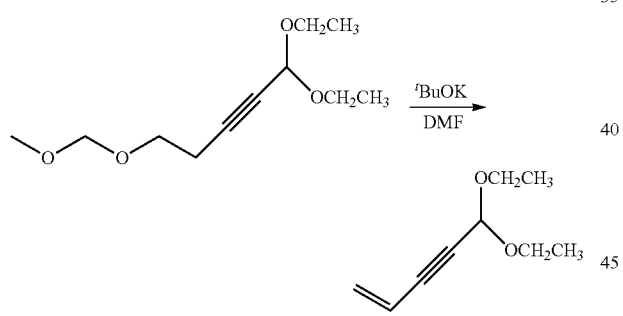

Potassium t-butoxide (17.08 g, 0.15 mol) and N,N-dimethylformamide (DMF) (78.92 g) were placed in a reactor at room temperature and stirred at from 10 to 15° C. for 40 minutes. Then, 1,1-diethoxy-5-(methoxymethoxy)-2-pentyne (3: $R^1$=Et, $R^2$=Et; Z=$CH_3OCH_2O$) (30.00 g, 0.14 mol, purity: 99.80%) was added dropwise to the reactor at 10 to 15° C. After the completion of the dropwise addition, the reaction mixture was stirred at from 10 to 20° C. for 3 hours. Next, water (83.04 g) was added to the reaction mixture, followed by phase separation and removal of the aqueous phase to obtain the organic phase. Then, the organic phase was concentrated at a reduced pressure and the residue was subjected to distillation at a reduced pressure (51.3 to 57.9° C./3.0 mmHg (0.40 kPa)) to obtain 5,5-diethoxy-1-penten-3-yne (1: $R^1$=Et, $R^2$=Et) (15.42 g, 0.072 mol, purity: 70.41%) in a yield of 50.87%.

The spectra data of 5,5-diethoxy-1-penten-3-yne (1: $R^1$=Et, $R^2$=Et) thus obtained were same as those in Example 1.

Example 3

Preparation of 5,5-diethoxy-1-penten-3-yne (1: $R^1$=Et, $R^2$=Et)

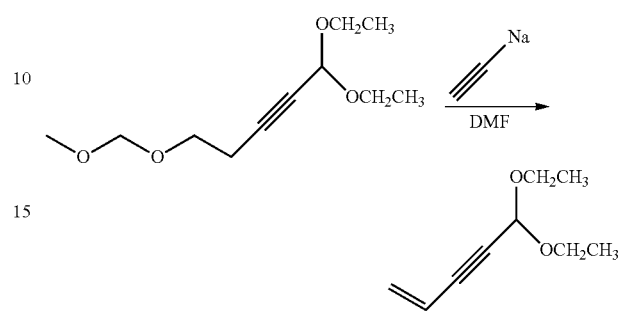

Sodium acetylide (7.31 g, 0.15 mol) and N,N-dimethylformamide (78.62 g) were placed in a reactor at room temperature and stirred at from 10 to 15° C. for 40 minutes. Then, 1,1-diethoxy-5-(methoxymethoxy)-2-pentyne (3: $R^1$=Et, $R^2$=Et; Z=$CH_3OCH_2O$) (30.00 g, 0.14 mol, purity: 99.80%) was added dropwise to the reactor at 10 to 15° C. After the completion of the dropwise addition, the reaction mixture was stirred at from 10 to 20° C. for 3 hours, and further at 60° C. for 2.5 hours. Next, water (83.04 g) was added to the reaction mixture, followed by phase separation and removal of the aqueous phase to obtain the organic phase. Then, the organic phase was concentrated at a reduced pressure and the residue was subjected to distillation at a reduce pressure (51.3 to 57.9° C./3.0 mmHg (0.40 kPa)) to obtain 5,5-diethoxy-1-penten-3-yne (1: $R^1$=Et, $R^2$=Et) (36.21 g, 0.026 mol, purity: 10.89%) in a yield of 18.48%.

The spectra data of 5,5-diethoxy-1-penten-3-yne (1: $R^1$=Et, $R^2$=Et) thus obtained were same as those in Example 1.

Example 4

Preparation of 5,5-dimethoxy-1-penten-3-yne (1: $R^1$=Me, $R^2$=Me)

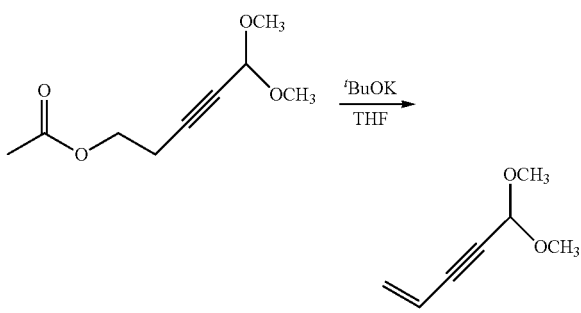

Potassium t-butoxide (23.19 g, 0.21 mol) and tetrahydrofuran (107.14 g) were placed in a reactor at room temperature and stirred at from 10 to 15° C. for 25 minutes. Then, 1,1-dimethoxy-5-acetyloxy-2-pentyne (3: $R^1$=Me, $R^2$=Me; Z=$CH_3C$(=O)—O) (34.99 g, 0.19 mol) was added dropwise to the reactor at 10 to 15° C. After the completion of the dropwise addition, the reaction mixture was stirred at from 10 to 20° C. for 1 hour. Next, water (112.74 g) was added to the reaction mixture, followed by phase separation and removal of the aqueous phase to obtain the organic phase. Then, the organic phase was concentrated at a reduced pressure and the residue was subjected to distillation at a reduced pressure (69.2 to 71.1° C./25.0 mmHg (3.3 kPa)) to obtain 5,5-dimethoxy-1-penten-3-yne (1: $R^1$=Me, $R^2$=Me) (20.73 g, 0.16 mol) in a yield of 87.44%.

The following is the spectrum data of 5,5-dimethoxy-1-penten-3-yne (1: $R^1$=Me, $R^2$=Me) thus produced.

[Nuclear magnetic resonance spectrum] $^1$H-NMR (500 MHz, CDCl$_3$): δ 3.37 (6H, s), 5.24 (1H, d, J=1.1 Hz), 5.55 (1H, dd, J=2.3 Hz, 11.1 Hz), 5.71 (1H, dd, J=2.3 HZ, 17.7 Hz), 5.82 (1H, ddd, J=1.2 Hz, 10.9 Hz, 17.9 Hz), $^{13}$C-NMR (125 MHz, CDCl$_3$): δ 52.42, 83.96, 84.30, 93.30, 115.82, 128.75.

[Mass spectrum] EI-Mass spectrum (70 eV): m/z 125 ($M^+$–1), 111, 95, 80, 65, 52.

[Infrared absorption spectrum] (NaCl): vmax 2938, 2905, 2831, 2230, 1603, 1358, 1343, 1192, 1162, 1099, 1056, 963, 901.

Example 5

Preparation of 5,5-dimethoxy-1-penten-3-yne (1: $R^1$=Me, $R^2$=Me)

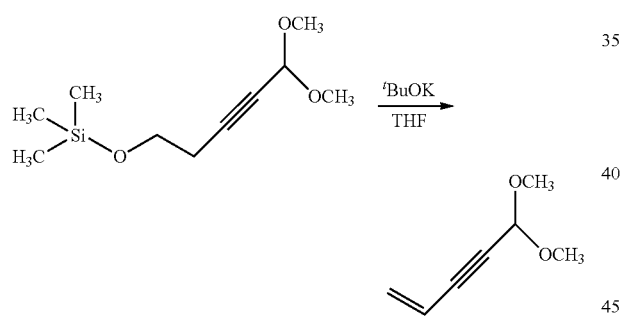

Potassium t-butoxide (23.61 g, 0.21 mol) and tetrahydrofuran (109.08 g) were placed in a reactor at room temperature and stirred at from 10 to 15° C. for 17 minutes. Then, 1,1-dimethoxy-5-trimethylsilyloxy-2-pentyne (3: $R^1$=Me, $R^2$=Me; Z=(CH$_3$)$_3$SiO) (41.39 g, 0.19 mol) was added dropwise to the reactor at from 10 to 15° C. After the completion of the dropwise addition, the reaction mixture was stirred at from 10 to 20° C. for 1.5 hours. Next, water (114.78 g) was added to the reaction mixture, followed by phase separation and removal of the aqueous phase to obtain the organic phase. Then, the organic phase was concentrated at a reduced pressure and the residue was subjected to distillation at a reduced pressure (69.2 to 7.1° C./25.0 mmHg (3.3 kPa)) to obtain 5,5-dimethoxy-1-penten-3-yne (1: $R^1$=Me, $R^2$=Me) (13.02 g, 0.10 mol) in a yield of 53.93%.

The spectra data of 5,5-dimethoxy-1-penten-3-yne (1: $R^1$=Me, $R^2$=Me) thus obtained were same as those in Example 4.

Example 6

Preparation of 5,5-dimethoxy-1-penten-3-yne (1: $R^1$=Me, $R^2$=Me)

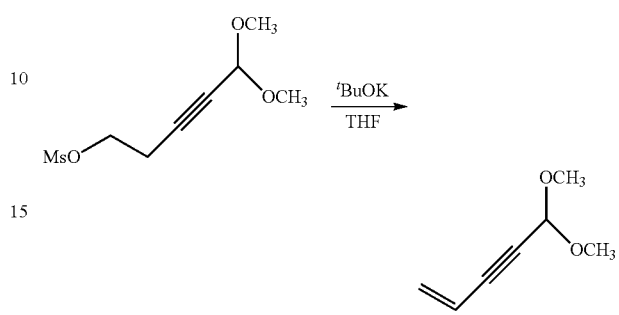

Potassium t-butoxide (23.96 g, 0.21 mol) and tetrahydrofuran (110.68 g) were placed in a reactor at room temperature and stirred at from 10 to 15° C. for 21 minutes. Then, 1,1-dimethoxy-5-methanesulfonyloxy-2-pentyne (3: $R^1$=Me, $R^2$=Me; Z=OMs (i.e., OSO$_2$CH$_3$)) (43.14 g, 0.19 mol) was added dropwise to the reactor at from 10 to 15° C. After the completion of the dropwise addition, the reaction mixture was stirred at from 10 to 20° C. for 1.5 hours. Next, water (116.46 g) was added to the reaction mixture, followed by phase separation and removal of the aqueous phase to obtain the organic phase. Then, the organic phase was concentrated at a reduced pressure and the residue was subjected to distillation at a reduced pressure (69.2 to 71.1° C./25.0 mmHg (3.3 kPa)) to obtain 5,5-dimethoxy-1-penten-3-yne (1: $R^1$=Me, $R^2$=Me) (14.22 g, 0.11 mol) in a yield of 58.05%.

The spectra data of 5,5-dimethoxy-1-penten-3-yne (1: $R^1$=Me, $R^2$=Me) thus obtained were same as those in Example 4.

Example 7

Preparation of 4-penten-2-ynal (2)

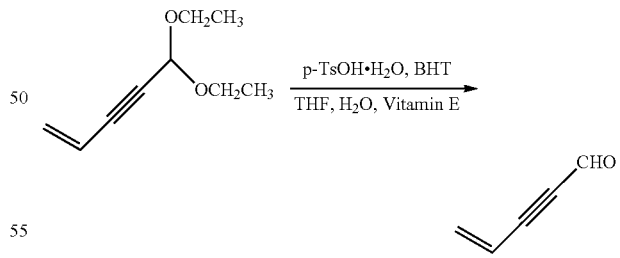

5,5-Diethoxy-1-penten-3-yne (1: $R^1$=Et, $R^2$=Et) (46.26 g, 0.30 mol) which had been prepared as in Example 1 and purified, vitamin E (0.20 g), dibutylhydroxyltoluene (BHT) (0.20 g), tetrahydrofuran (150.00 g) and water (150.00 g) were placed in a reactor at room temperature and stirred at from 20 to 30° C. for 5 minutes. Then, p-toluenesulfonic acid monohydrate (p-TsOH.H$_2$O) (2.91 g, 0.015 mol) was added to the reactor at from 20 to 30° C. and stirred at from 60 to 65° C. for 3 hours. Next, sodium hydrogen carbonate (2.52 g) and toluene (272.31 g: including 40 g of toluene for taking up sodium hydrogen carbonate from a vessel) were added to the reaction mixture, followed by phase separation and removal of the aqueous phase to obtain the organic phase. Then, the organic phase was concentrated at a reduced pressure to obtain 4-penten-2-ynal (2) (17.93 g, 0.22 mol) in a mixed solvent of toluene (234.36 g) and tetrahydrofuran (93.53 g) in a yield of 74.63%. The amounts of toluene and tetrahydrofuran in the mixture were determined by GC and NMR.

The following is the spectrum data of 4-penten-2-ynal (2) thus produced.

[Nuclear magnetic resonance spectrum] $^1$H-NMR (500 MHz, CDCl$_3$): δ 9.35 (1H, d, J=0.7 Hz), 6.08 (1H, dd, J=17.2 Hz, 2.3 Hz), 6.01 (1H, ddd, J=17.4 Hz, 10.9 Hz, 0.7 Hz), 5.91 (1H, dd, J=10.9 Hz, 2.3 Hz), $^{13}$C-NMR (125 MHz, CDCl$_3$): δ 88.28, 93.02, 114.75, 134.25, 176.70.

[Mass spectrum] EI-Mass spectrum (70 eV): m/z 80 (M$^+$), 61, 52.

[Infrared absorption spectrum] (NaCl): vmax 2977, 2873, 2210, 2172, 1664, 1162, 1080, 1035, 972, 947, 798.

Reference Example 1

Preparation of 9,13-tetradecadien-11-ynal (6)

of the dropwise addition, the reaction mixture was stirred at from 20 to 30° C. for 2 hours. Next, a solution of sodium chloride (45.47 g) in water (464.65 g) was added to the reaction mixture, followed by phase separation and removal of the aqueous phase to obtain the organic phase. Then, the organic phase was concentrated at a reduced pressure to obtain a crude product, 14,14-diethoxy-1,5-tetradecadien-3-yne (5: R$^3$=Et, R$^4$=Et), (74.22 g, 0.18 mol, purity: 68.06%, E/Z=26/74) in a crude yield of 90.02%. The crude product contained toluene, triphenylphosphine, and triphenylphosphine oxide as impurities.

Subsequently, the crude product, 14,14-diethoxy-1,5-tetradecadien-3-yne (7: R$^3$=Et, R$^4$=Et) thus obtained, (74.22 g, 0.18 mol, purity: 68.06%, E/Z=26/74), oxalic acid dihydrate (68.61 g, 0.54 mol), tetrahydrofuran (181.40 g), and pure water (181.40 g) were added to a reactor and stirred at from 60 to 65° C. for 4 hours. Then, the reaction mixture was cooled to 50° C., and hexane (53.35 g) was added, and the reaction mixture was stirred for 30 minutes. After completion of the stirring, the reaction mixture was allowed to stand for phase separation, followed by removal of the aqueous phase to obtain the organic phase. Then, the organic phase was concentrated at a reduced pressure and the residue was subjected to distillation at a reduced pressure (125.1 to

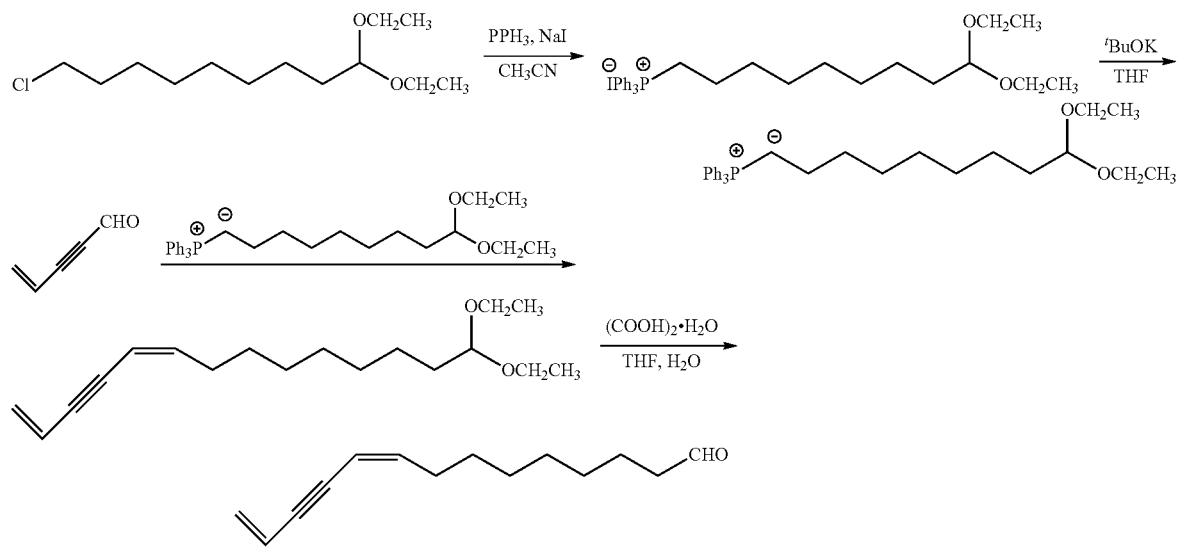

9-Chloro-1,1-diethoxynonane (7: X=Cl; R$^1$=Et, R$^2$=Et) (90.29 g, 0.36 mol), triphenylphosphine (8: Ar=Ph) (94.65 g, 0.36 mol), sodium iodide (58.46 g, 0.39 mol), potassium carbonate (2.90 g, 0.021 mol), and acetonitrile (192.45 g) were placed in a reactor at room temperature and stirred at from 75 to 85° C. for 15 hours to obtain 9,9-diethoxynonyltriphenylphosphonium iodide (9: Y=I; Ar=Ph; R$^3$=Et, R$^4$=Et). Then, tetrahydrofuran (346.14 g) was added dropwise to the reactor at 30 to 40° C. After the completion of the dropwise addition, the reaction mixture was cooled to −5 to 10° C. Next, potassium t-butoxide (38.71 g, 0.35 mol) was added and stirred for 1 hour to obtain triphenylphosphonium 9,9-diethoxynonylide (4: Ar=Ph; R$^3$=Et, R$^4$=Et).

Next, 4-penten-2-ynal (2) (16.14 g, 0.20 mol) which had been prepared as in Example 7 in a mixed liquid of toluene (220.99 g) and tetrahydrofuran (78.56 g) was added dropwise to the reactor at from −5 to 5° C. After the completion 133.1° C./3.0 mmHg (0.40 kPa)) to obtain 9,13-tetradecadien-11-ynal (6) (31.40 g, 0.15 mol, purity: 96.03%, E/Z=25/75) in a yield of 73.25% of the two steps.

The following is the spectrum data of 9,13-tetradecadien-11-ynal (6) thus produced.

[Nuclear magnetic resonance spectrum] $^1$H-NMR (500 MHz, CDCl$_3$): δ 1.27-1.35 (6H, m), 1.40 (2H, br. quint, J=6.5 Hz), 1.61 (2H, br. quint, J=6.9 Hz), 2.30 (2H, ddt, J=1.5 Hz, 7.3 Hz, 7.3 Hz), 2.40 (2H, dt, J=1.9 Hz, 7.3 Hz), 5.44 (1H, dd, J=11.2 Hz, 1.9 Hz), 5.55 (1H, br. dd, J=10.7 Hz, 1.9 Hz), 5.60 (1H, dd, J=17.6 Hz, 1.9 Hz), 5.86-5.97 (2H, m), 9.75 (1H, t, J=1.9 Hz); $^{13}$C-NMR (125 MHz, CDCl$_3$): δ 21.99, 28.63, 28.80, 29.01, 29.05, 30.14, 43.84, 86.98, 92.16, 108.91, 117.36, 126.03, 144.18, 202.80.

[Mass spectrum] EI-Mass spectrum (70 eV): m/z 204 (M$^+$), 175, 161, 147, 133, 119, 105, 91, 78, 65, 53.

[Infrared absorption spectrum](NaCl): vmax 2929, 2856, 1725, 1464, 1413, 1392, 972, 918, 739.

The invention claimed is:

1. A process for preparing 4-penten-2-ynal of the following formula (2):

$$CH_2=CHC\equiv CCHO \quad (2)$$

the process comprising a step of
hydrolyzing a 5,5-dialkoxy-1-penten-3-yne compound of the following general formula (1):

$$CH_2=CHC\equiv CCH(OR^1)(OR^2) \quad (1)$$

wherein $R^1$ and $R^2$ represent, independently of each other, a monovalent hydrocarbon group having 1 to 15 carbon atoms, or $R^1$ and $R^2$ may be bonded to each other to form a divalent hydrocarbon group, $R^1$-$R^2$, having from 2 to 10 carbon atoms,
in the presence of p-toluenesulfonic acid or oxalic acid to obtain 4-penten-2-ynal (2).

2. A process for preparing 4-penten-2-ynal of the following formula (2):

$$CH_2=CHC\equiv CCHO \quad (2)$$

the process comprising a step of
eliminating a leaving group of a 2-ynal acetal compound of the following general formula (3):

$$Z(CH_2)_2C\equiv CCH(OR^1)(OR^2) \quad (3)$$

wherein $R^1$ and $R^2$ represent, independently of each other, a monovalent hydrocarbon group having 1 to 15 carbon atoms, or $R^1$ and $R^2$ may be bonded to each other to form a divalent hydrocarbon group, $R^1$-$R^2$, having from 2 to 10 carbon atoms, and Z represents a leaving group selected from the group consisting of an alkoxy group having 1 to 12 carbon atoms, an acyloxy group having 1 to 10 carbon atoms, a silyloxy group having 3 to 20 carbon atoms, an alkanesulfonyloxy group having 1 to 10 carbon atoms, an arenesulfonyloxy group having 6 to 20 carbon atoms, and a halogen atom,
in the presence of a base to obtain a 5,5-dialkoxy-1-penten-3-yne compound (1) of the following general formula (1):

$$CH_2=CHC\equiv CCH(OR^1)(OR^2) \quad (1)$$

wherein $R^1$ and $R^2$ are as defined above; and
hydrolyzing the 5,5-dialkoxy-1-penten-3-yne compound (1) to obtain 4-penten-2-ynal (2).

3. The process for preparing 4-penten-2-ynal (2) according to claim 1, wherein the hydrolyzation is carried out in the presence of p-toluenesulfonic acid.

4. The process for preparing 4-penten-2-ynal (2) according to claim 1, wherein $R^1$ and $R^2$ are each independently a monovalent hydrocarbon group having 1 to 8 carbon atoms.

5. The process for preparing 4-penten-2-ynal (2) according to claim 1, wherein $R^1$ and $R^2$ are each independently a monovalent hydrocarbon group having 1 to 4 carbon atoms.

6. The process for preparing 4-penten-2-ynal (2) according to claim 1, wherein $R^1$ and $R^2$ are bonded to each other to form a divalent hydrocarbon group, $R^1$-$R^2$, having from 2 to 10 carbon atoms.

* * * * *

UNITED STATES PATENT AND TRADEMARK OFFICE
CERTIFICATE OF CORRECTION

PATENT NO. : 11,097,999 B2
APPLICATION NO. : 17/010236
DATED : August 24, 2021
INVENTOR(S) : Miyake et al.

It is certified that error appears in the above-identified patent and that said Letters Patent is hereby corrected as shown below:

In the Specification

Column 16, Line 22: Please correct "(78.62 g)" to read -- (78.92 g) --

Column 18, Line 64: Please correct "(p-TsOH.H$_2$O)" to read -- (p-TsOH·H$_2$O) --

Signed and Sealed this
Twenty-eighth Day of June, 2022

*Katherine Kelly Vidal*
Katherine Kelly Vidal
*Director of the United States Patent and Trademark Office*